United States Patent [19]

Armentrout et al.

[11] 4,124,141
[45] Nov. 7, 1978

[54] STERILE CONTAINER

[76] Inventors: James L. Armentrout, 21 Barlovento Ct., Newport Beach, Calif. 92663; George H. Schneider, 22475 Overlake Dr., El Toro, Calif. 92630

[21] Appl. No.: 814,159

[22] Filed: Jul. 11, 1977

[51] Int. Cl.² ............................................. B65D 43/02
[52] U.S. Cl. ............................ 220/306; 206/439; 220/354; 220/359; 220/371; 220/DIG. 27; 229/43
[58] Field of Search ............... 206/439, 210, 435; 220/306, 354, 359, 371, 372, DIG. 27, 307; 229/43

[56] References Cited

U.S. PATENT DOCUMENTS

| 606,838 | 7/1898 | Heins | 220/354 |
|---|---|---|---|
| 2,084,084 | 6/1937 | Greer | 220/354 |
| 2,603,308 | 7/1952 | McCall | 220/372 |
| 2,675,093 | 4/1954 | McCall et al. | 220/371 |
| 3,044,610 | 7/1962 | Tupper | 220/306 |
| 3,321,104 | 5/1967 | Edwards | 220/306 |
| 3,371,848 | 3/1968 | Ward et al. | 229/45 |
| 3,546,853 | 12/1970 | Claar | 220/371 |
| 3,550,808 | 12/1970 | Mounts | 220/359 |
| 3,566,946 | 3/1971 | MacDonald | 220/306 |
| 4,022,324 | 5/1977 | Schuster | 206/210 |

FOREIGN PATENT DOCUMENTS

| 1,264,539 | 5/1961 | France | 220/371 |
|---|---|---|---|
| 105,963 | 11/1942 | Sweden | 220/354 |
| 507,941 | 6/1939 | United Kingdom | 220/371 |

Primary Examiner—William Price
Assistant Examiner—Bruce H. Bernstein
Attorney, Agent, or Firm—Charles H. Schwartz

[57] ABSTRACT

A sterile container, including a container body having an open end for receiving an item to be maintained in a sterile environment and with the container body including a flange portion extending around the entire container body at the open end, a sealing cavity formed within the flange portion of the container body and extending throughout the length of the flange portion and with the cavity including an opening having a particular dimension across the opening and with at least a portion of the cavity within the cavity having a larger dimension across the cavity than the particular dimension across the opening, a cover for closing the open end of the container body and with the cover including a flange portion extending around the entire cover, and a sealing cavity formed within the flange portion of the cover and with one of the sealing cavities nested within the other when the cover seals the open end of the container body and with the shape of the sealing cavity in the flange portion of the cover complementary to the shape of the sealing cavity in the flange portion of the container body.

15 Claims, 15 Drawing Figures

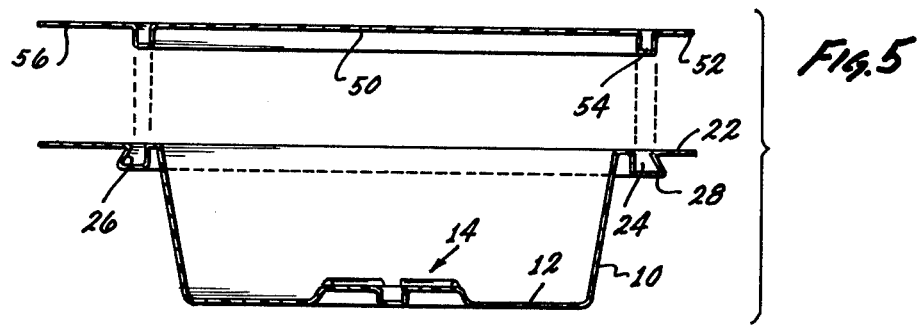
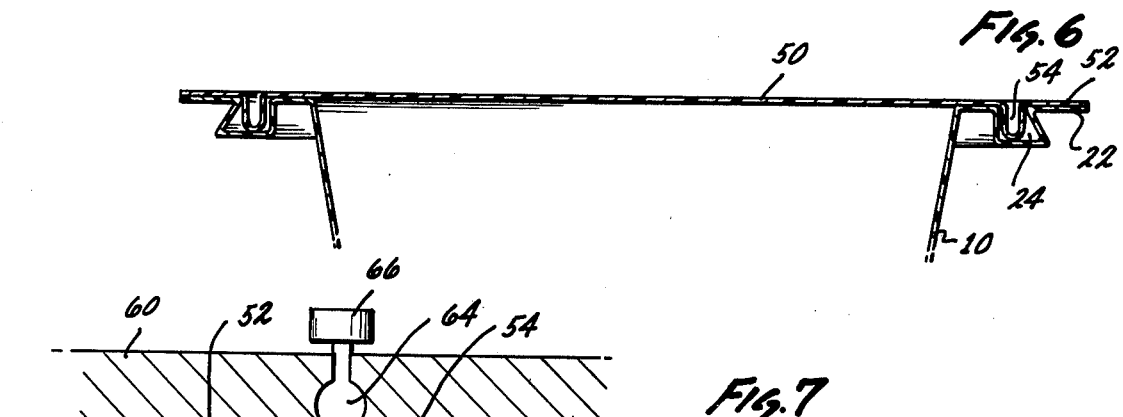
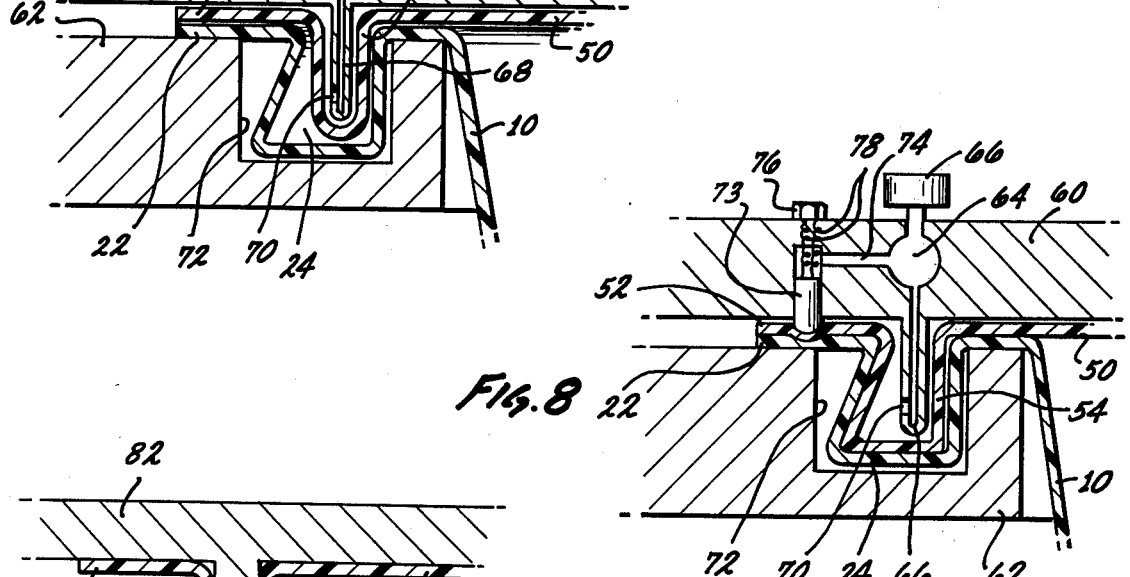
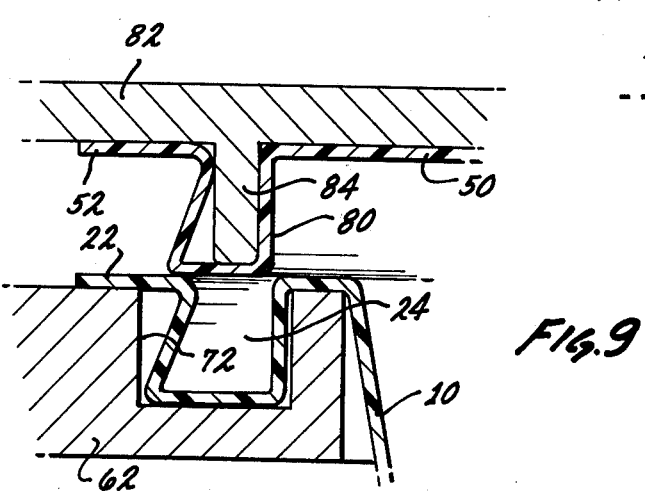

STERILE CONTAINER

The present invention relates to a container for use in packaging an instrument or device within the container and for maintaining a sterile environment within the container. The invention also relates to a method of sealing such container wherein the container can be opened in an aseptic fashion without contaminating the instrument or device within the container. The container may also include an opening providing for a gas pathway to aid in the sterilization of the instrument or device within the container. The pathway includes means operating as a bacterial barrier against the intrusion of bacteria or other foreign materials during transport and storage of the container enclosing the sterile instrument or device. Sterile containers of the type provided for in the present invention are normally used in medical applications but it is to be appreciated that the sterile container may be used for other types of applications.

Normally medical instruments or devices, when packaged in prior art sterile containers, are provided within containers which are generally sealed or closed by one of two methods. In a first prior art method, the container is closed by heat sealing a coated paperboard, paper or other porous membrane to an outwardly extending flange of a container body and with the porous membrane providing a cover and a gas pathway for the opening into the container body.

In a second prior art method, the container includes some form of cover which adheres to the container body by some mechanical arrangement such as a friction fit between the container body and cover or through the use of a mechanical lock or other mechanical means. This type of container is broadly of the same type used in food packaging or in beverage cups and this type of container is normally resealable. It is appreciated that in the packaging field there are numerous ways for providing for a container which is sealed but in most instances these types of containers are not acceptable for the packaging of medical instruments or devices and would not provide for the sterilization of or provide a proper bacterial barrier for the instrument or device within the container.

In the packaging of sterile medical instruments or devices, a number of special conditions must be met by the packaging. Specifically, the package must be easy to open and the cover of the package must separate cleanly from the package upon opening. This clean separation is to prevent the exposure of ragged fibers, torn portions or any delaminating of particles such as from the membrane, all of which might contaminate the instrument or device as it is removed from the container. In addition, the container is normally not reclosable or resealable because in the event of an inadvertent opening of the package, the instrument or device would be exposed to atmosphere and could become contaminated. Therefore, it is desirable that the package should not be reclosable since opening and then reclosing the package could present a danger to a patient if the package is reopened again and used without knowledge of the prior opening. In addition, the package should be constructed of materials that are relatively free of fibers, plastic shards or other foreign matter, and should be capable of being opened at the point of use without contributing fibers, dust, contaminants or other particulate matter to the instruments or devices contained within the package.

The prior art type of heat sealed packages normally do not meet the conditions described above. Since heat sealing is a function of heat, pressure and the dwell time of the heat and pressure applied, any variation of any of these parameters can adversely affect the final seal. For example, if the heat and pressure or the dwell time is too great, a hard seal may occur which makes it impossible to open the package without delaminating or tearing the cover. Such a tearing of the cover can result in ragged edges that may brush and contaminate the item contained in the package or the tearing can contribute particulate matter to the inside of the package in the form of fibers, dust or coating particles. Any of this particulate matter within the interior of the package can compromise the device or instrument contained within and make the device or instrument unfit for use.

As an alternative, an adverse condition may also occur if the heat or pressure or dwell time is too low. These conditions may result in packages wherein the covers are attached too lightly so that the packages may be subject to premature opening during the vacuum and pressure phases of the sterilization process, or the package may be opened merely by flexing, or the package may even become opened during vibration which can occur during shipment or storage.

In the packages which use the heat sealing membrane for closure, a considerable force may be required to remove the membrane cover. For example, a force having a magnitude of one and-a-half to two pounds along the entire length of the sealed area may be required. Packages of this type may have outwardly extending tabs which are grasped in opposing hands and with the container body and membrane cover separated by force so as to peel the membrane cover away from the body.

Initially, as the separating force is applied, some distortion may occur in both the container body and the membrane cover. In addition, as the separating force is continuously applied and as the distance between the separating tabs increases around the periphery of the container as the cover is being peeled, the distortion of both the container body and membrane cover will also increase. This may provide for a gross distortion of the container, especially when the dimensions are fairly large. In such a case, the container body may become so distorted that the body will no longer contain the items within the body and these items may be spilled out of the container making them useless as sterile items. For example, in some types of packages, a multiplicity of devices are within the container so that the package has a large dimension. The above-described problem may occur with such packages. As a specific example, such a package may contain all of the items necessary for a spinal procedure or all of the items necessary for an angiogram.

Other adverse factors may also affect prior art heat sealed packages so as to result in package failure. For example, variations in the solid contents of the package sealant may result in a seal which is either too hard or too soft. In addition, variations in the fiber structure of the paper or the membrane used may affect the heat seal. Solvents may become entrapped during the coating of the membrane with the package sealant which solvents could affect the seal. Finally, aging of the heat seal during storage of the coated membrane prior to its use as a cover may also adversely affect the final heat seal.

The most serious problem with the prior art packages used to provide for sterile containers is the production of particulate matter during either the manufacture of the package, the sealing of the package, or during the opening of the package. This particulate matter is generally defined as any foreign matter dust, plastic or paper flakes or fibers, coating flakes or fibers, oil, grease or other foreign substances which might tend to contaminate the device or instrument within the package.

As an example, particulate matter can occur from numerous sources when using membrane covers which are normally closed by heat sealing. For example, particulate matter may occur from the heat sealant or coating which acts as the heat sealant which may during sealing tend to flake and chip and which may deposit these flakes or chips on the instrument or device contained in the package. Also, particulate matter may occur by fibering or delamination of the membrane cover as the package is opened. In addition, the particulate matter may occur by the generation of fiber or dust from the membrane cover by reason of twisting or distortion of the membrane or by vibration during shipment or storage.

The present invention overcomes the various difficulties described above by providing for a container including a package body and a cover wherein the body includes a circumferential flange having an annular descending cavity which extends around the entire length of the flange. The opening into the cavity is a lesser dimension than the base of the descending cavity. The cover member includes a complementary circumferential flange and a complementary cavity member which, when the cover and body are mated, provides for the cavity portion of the flange of the cover nested within the cavity portion of the flange of the body and with a laminar contact between the walls of the cavities. Since the cross-sectional dimensions of the cavities increase in the descending direction, this tends to lock the cavities together since the opening portion of the cavities is of a lesser dimension than the base portion of the cavities. The cover is therefore sealed across the body to provide for the sterile enclosed area within the sealed combination of the body and cover members.

In one embodiment of the invention, the cavity portion of the cover member is heat formed to the desired complementary configuration within the cavity portion of the body member which had been preformed to the desired configuration. In a second embodiment of the invention, the cavity portions of the cover and the body members have been preformed to the desired complementary configurations and with the dimensions of either one or both of the cavities temporarily distorted so as to nest one cavity within the other. Since both the cover and the body members are made of a flexible plastic the materials will then return to their preformed configurations with one cavity portion locked within the other.

An additional aspect of the present invention is in the provision of a gas pathway into the interior of the container and with the pathway including an integral bacterial barrier portion of the container. As an example, this portion may be formed as a recess in the body portion of the container having a first smaller portion for receiving a first bacterial barrier. This barrier may be provided by a rod of cellulosic fibers. A second bacterial barrier may be provided in a second portion of the recess. The second bacterial barrier may be provided by a porous material formed as a flat member so as to lock the first bacterial barrier member in position. This type of gas pathway incorporates a redundant filtering system which provides for the maximum of safety in the filtering of the gas transmitted into and out of the package during the sterilizing process. This bacterial barrier then acts to provide for a barrier against the introduction of bacteria during shipment and storage of the sterile container containing the device or instrument.

a clearer understanding of the invention will be had with reference to the following description and drawings wherein FIG. 1 is a top elevational view of a container body constructed in accordance with the teachings of the present invention;

FIG. 5 is a cross-sectional view of the body member and the first embodiment of the cover shown prior to fitting the cover to the body;

FIG. 6 illustrates the first embodiment of the cover member displaced on the body member;

FIG. 7 illustrates a portion of the cover and body members and including means for providing a seal between the cover and body members;

FIG. 8 is a portion of the cover and body members sealed with the means of FIG. 7 and including additional means for providing a seal between the cover and body members;

FIG. 9 illustrates a portion of the body member and a second embodiment of the cover member and including means for sealing the cover member to the body member;

Figure 1:
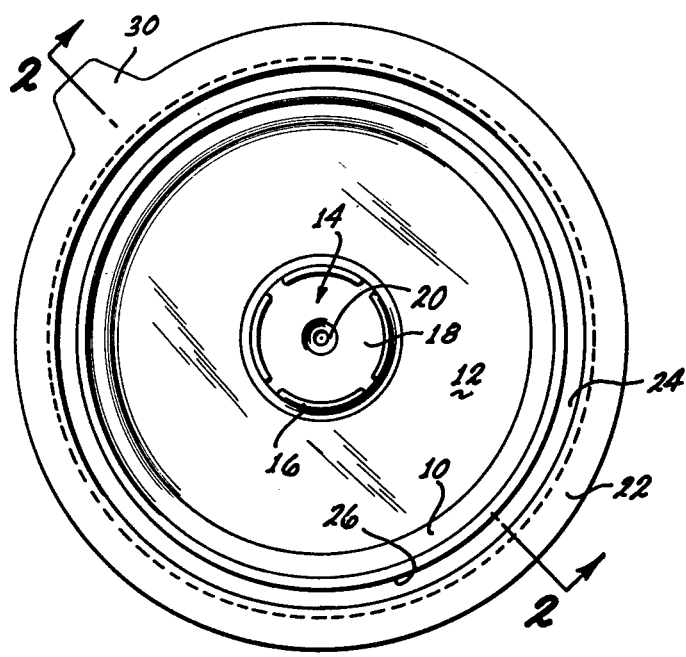
Figure 2:
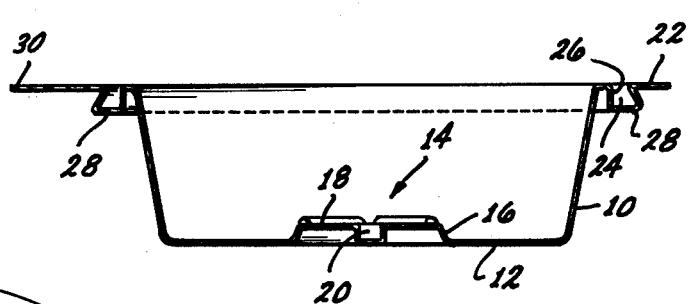
FIG. 2 is a side cross-sectional view of the container body of FIG. 1.

As shown in FIGS. 1 and 2, the container body is formed as a tray or dish having a sidewall 10, a bottom 12 including a portion 14 formed to provide for a gas pathway. Specifically, the portion 14 includes an upstanding wall 16 folded over to form a slight depression 18 leading to a recess 20 to form the gas pathway. As will be described in a later portion of this specification, the recess 20 receives a filter and the depression 18 receives a flat porous filter membrane.

The sidewall 10 has extending outwardly around its upper periphery a flange 22. The flange 22 includes an annular descending cavity 24 and with an opening 26 to the cavity of a smaller dimension than a bottom wall 28 of the cavity. It can be seen that the opening 26 into the cavity is of lesser cross-sectional dimension than the bottom wall 28 or the terminating base of the cavity so that the sidewalls of the cavity expands outwardly from a small opening to the base portion. The use of this particular shape for the cavity 24 provides for the improved sealing of the sterile container of the present invention. A lift tab 30 extends from the flange 22 and is used during the removal of a cover portion from the container body.

Figure 3:
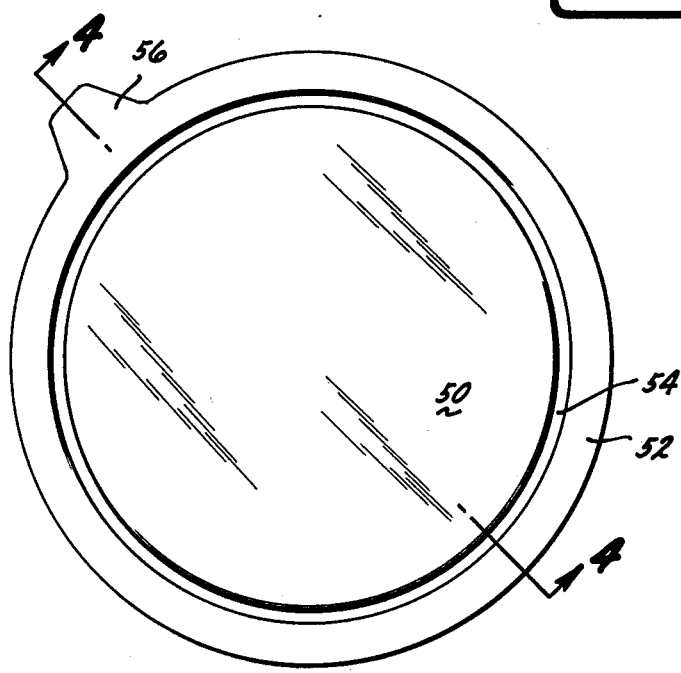
FIG. 3 is a top elevational view of one embodiment of a container cover used in conjunction with the container body to form a sterile package.
Figure 4:
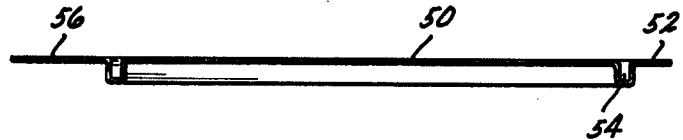
FIG. 4 is a cross-sectional view of the first embodiment of the container cover of FIG. 3.

FIGS. 3 and 4 illustrate a first embodiment of a cover which may be used with the container body as shown in FIGS. 1 and 2. Specifically, the cover includes a flat portion 50 which serves as the main cover for the open end of the container body shown in FIGS. 1 and 2. A flanged portion 52 extends peripherally around the exterior of the cover and with a descending cavity portion 54 formed intermediate the flat portion 50 and the flanged portion 52. The flanged portion 52 includes an integral lift tab 56 to aid in the removal of the cover as shown in FIGS. 3 and 4 from the container body as shown in FIGS. 1 and 2 when the cover is sealed across the opening in the container body.

FIGS. 5 and 6 illustrate the interrelationship of the cover and the container body prior to sealing. As shown in FIG. 5, the cover member may be positioned above the container body prior to sealing but after a particular device or instrument is placed in the container body. It is also to be appreciated that the various filter and membrane members used to form the bacterial barrier in the gas pathway provided by the portion 14 have been inserted in position prior to the placing of the device or instrument within the container body. When all of the desired items are placed within the container body then the cover may be positioned as shown in FIG. 6 wherein the descending cavity 54 of the cover will be received within the descending cavity 24 of the container body. At this time, the cover and body are ready for sealing the cover across the container body.

Means for providing for the sealing is shown in FIG. 7 wherein the cover has a descending cavity portion 54 as shown in FIGS. 3 and 4. In FIG. 7 a fragmentary view showing essentially the interrelationship of the descending cavity portions 54 and 24 is shown. In order to provide for the sealing of the cavity portion 54 within the cavity portion 24, a pair of clamping members 60 and 62 are used. Specifically, the clamping member 60 may be a flat plate member which covers the entire flat cover member 50 including the flanged portion 52. The clamping member 60 includes an annular opening 64 which extends around and is surrounded by the clamping member 60. This annular opening 64 communicates with a source 66 of hot air under pressure. In addition, extending downwardly from the clamp plate 60 and communicating with the opening 64, is an annular ring nozzle 68 which fits within the descending cavity 54. An opening 70 in the ring nozzle 68 communicates with the interior of the descending cavity 54.

The descending cavity 24 is received within a recess 72 in the bottom clamp plate 62. The bottom clamp plate 62 extends around the container body and supports the flanged portion 22 and, as shown in FIG. 7, receives the descending cavity portion 24 within the recess 72. The flanged portions 52 and 22 are therefore clamped together by the clamp plates 60 and 62. As shown in FIG. 8, hot air under pressure may be supplied through the annular opening 64 into the annular ring nozzle 66 and through the opening 70 to the interior of the descending cavity 54.

The material of the cover and the descending cavity 54 would be constructed of a thermoplastic material. The combination of the hot air and the pressure differential created by the hot air, as introduced into the descending cavity 54, provides for the distortion of the descending cavity 54 to conform to the configuration of the descending cavity 24 formed in the container body. Because the dimension at the base of the descending cavity 24 is greater than at the opening, the descending cavity 54 will be formed to a complementary shape within the cavity 24, as shown in FIG. 8, and the cavities 54 and 24 will be locked one within the other because of this dimensional difference.

It is to be appreciated that the cavities may be reversed and with the cavity 54 preformed and the cavity 24 formed around cavity 54 using hot air under pressure in the clamp 62. In addition, the shape of the cavities may be different than that shown, as long as the sidewall extends outwardly in the direction away from the open end of the cavity. Also the cavities may be positioned upwardly rather than downwardly.

FIG 8 also shows the use of an auxiliary method of providing for an additional means of fastening the flanged portions 22 and 52 together so as to operate as a secondary safety seal. As seen in FIG. 8, this secondary safey seal may be provided by a heat conductive punch 73 which is coupled through orifice 75 to the annular opening 64. In addition, a source of electrical current 76 provides electricity through wire 78 for heating the punch 73. When the hot air under pressure from source 66 is supplied to the annular opening 64, this also provides for the air under pressure through orifice 74 to drive the punch 73 down into engagement with the flange 52. This produces a heat staking of the flange 52 to the flange 22. If a number of punches 73 are used, this heat staking may occur at a rally of points around the periphery of the package flange or a continuous punch may be used to provide a continuous line of heat staking. When the cover is removed from the package body, the breaking apart of these heat staked points or the heat staked line reveals that the container has been opened and would eliminate any reclosure of the container. Also the use of this heat staking additionally prevents a premature opening of the cover from the container body.

Figure 10:
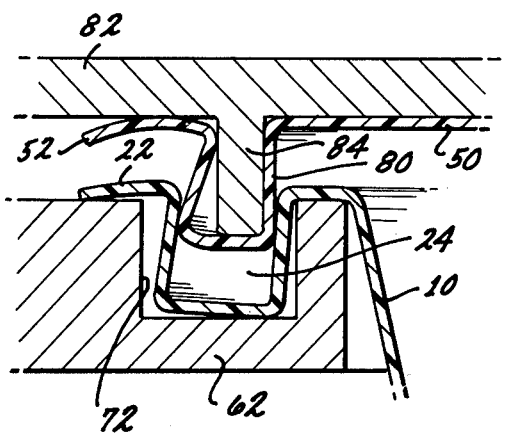
FIG. 10 illustrates the structure of FIG. 9 with the cover member partially inserted to seal the open end of the body member.

FIGS. 9 and 10 illustrate a second embodiment of the cover for use with a container body of the same type as described above. Specifically, in FIGS. 9 and 10, the container body including the sidewall 10 with a flange 22 and the annularly descending cavity 24 is positioned within the clamping member 62 having the recess 72. The cover member includes the flat cover portion 50 and the flange 52 and additionally includes an annularly descending channel 80. As shown in FIG. 9, this cavity 80 is formed with a complementary configuration to fit within the cavity 24 without the use of hot air under pressure as with the structure shown in FIGS. 7 and 8. A top clamp 82 including a ring portion 84 which extends downwardly is positioned over the cover member. The ring portion 84 fits within the cavity 80.

Figure 11:
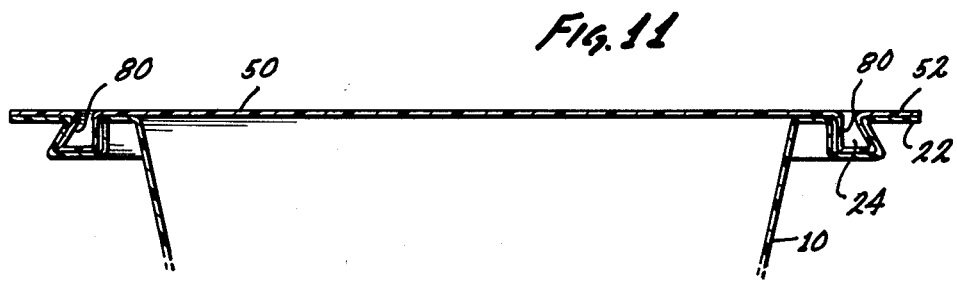
FIG. 11 illustrates a sterile container constructed of a body member and either of the first or second embodiment of the cover members.

Upon the application of force pushing the clamp 82 toward the clamp 62, this force provides for a distortion of the lower portion of the cavity 80 and the upper portion of the cavity 24. As shown in FIG. 10, this distortion is sufficient so that the sidewalls of the upper cavity 80 will be received through the opening of the lower cavity 24 so that the cavity 80 will become nested within a cavity 24 to form the seal as shown in FIG. 11. As can be seen in FIG. 11, the cover member is sealed across the container body with the cavity 80 interlocked within the cavity 24. Actually the resultant structure as shown in FIG. 11 is essentially the same for both embodiments of the invention.

Figure 12:
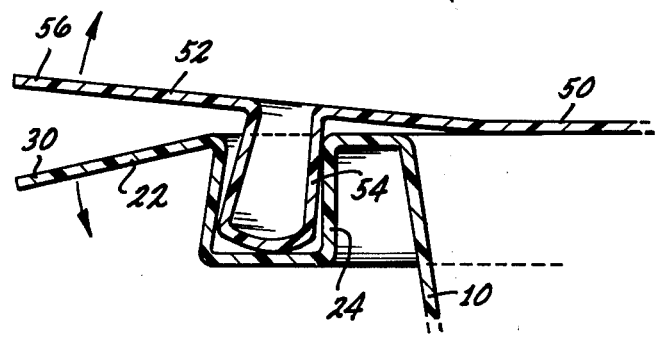
FIG. 12 illustrates a method of removing the cover member from the body member of the sealed container of FIG. 11.

FIG. 12 illustrates the method by which the cover is removed from the container body. As shown in FIG. 12 the lift tabs 56 and 30 which extend from the flanges 52 and 22 may be separated as indicated by the arrows. When the tabs are separated, this also separates the flanges and the opening of the cavity 24 will distort and become greater which will allow the cavity 54 to pass through the expanded opening of the cavity 24. Once a portion of the cavity 54 is removed from a portion of the cavity 24, this will allow the cover to be peeled off the container body. Actually, once a portion of the cavity 54 is removed, the laminar contact between the two cavities is relieved and a further pulling of the tab 56 allows for the cover to be removed with virtually no distortion of the container body. This is important since it allows the contents of the container to remain in their proper position and not be spilled onto the floor as could happen with the prior art heat sealed packages.

Figure 13:
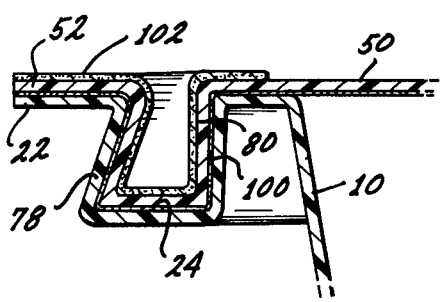
FIGS. 13 and 14 illustrate the use of additional means for providing a seal between the cover member and the body member of the sterile container of the present invention.

FIG. 13 illustrates additional means which may be used to provide for an additional sealing between the cover and the body member. For example, an adhesive coating 100 may be positioned between the cavities 24 and 80, by precoating the outside of the cavity 80 or the inside of the cavity 24. When the cavities 24 and 80 are positioned with cavity 80 nested within cavity 24, the adhesive 100 would act as a further seal between these cavity portions. For example, the adhesive may be applied in a liquid state and then may dry to form an adhesive bonding between the cavities 24 and 80.

As another means of locking the cavity 80 within the cavity 24, an exterior plug member 102 may be positioned within the cavity 80 to provide additional force to maintain the cavity 80 in laminar contact with the cavity 24. As an alternative as shown in FIG. 14, an O-ring may be inserted between the cavities so as to provide an additional sealing pressure between the cavity 80 and the cavity 24.

Figure 14:
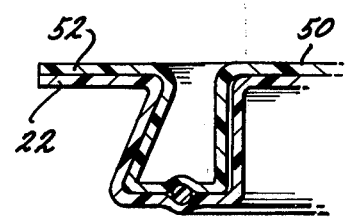
Figure 15:
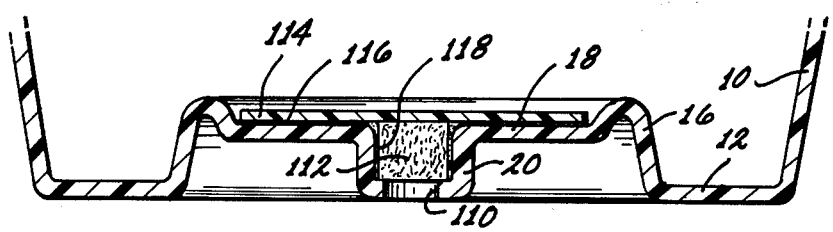
FIG. 15 illustrates a detail of a gas pathway including a bacterial barrier for use in sterilization of instruments or devices within the sterile container of the present invention.

FIG. 14 illustrates the structure provided at the bottom of the container body 12 to act as a gas pathway including a bacterial barrier. Specifically, as shown in FIG. 2 and in FIG. 14, the upstanding wall portion 16 dips down at position 18 to form a small recess. A further recess portion is formed by wall 20. An opening 110 provides for access to the interior of the container body for use as a gas pathway during sterilization of the contents within the container.

The primary bacterial barrier of the container is provided by a rod 112 of filter material such as a rod of cellulosic fibers which acts as a filter and a barrier for bacteria. A secondary bacterial barrier is provided by a flat porous membrane 114 which membrane may be formed from a filter paper and with the membrane 114 positioned within the slight recess 18 and over the rod 112. The membrane 114 may be held in position by an adhesive layer 116 within the slightly recessed portion 18. It can be seen that the adhesive maintains the membrane 114 in position and the membrane locks the rod 112 in position. In addition, an adhesive layer 118 is positioned around the filter rod 112 within the well to also maintain the rod in position and to guard against dust penetration around the vertical edges of the filter rod. The use of both a primary and secondary bacterial barrier provide for a redundant filtering system which provides the maximum of safety in filtering any air or gas transmitted in and out of the package during the sterilization process. In addition, after sterilization the use of the primary and secondary filtering system also provides for a redundent bacterial barrier for the container during shipment and storage of the sealed container and the contents therein. It is to be appreciated that the gas pathway may be formed in other wall portions of the container and may even be provided in the cover.

It is also to be appreciated that any heat formable plastic may be used in making the package, and any known method of heat forming, such as thermoforming, injection molding, pressure or transfer molding may be used to manufacture the package.

Although the invention has been described with reference to particular embodiments, it is to be appreciated that various adaptations and modifications may be made and the invention is only to be limited by the appended claims.

We claim:

1. A sterile container, including
    a container having side walls disposed in a closed loop and having a closed bottom end and having an open top end for receiving an item to be maintained in a sterile environment and formed from a heat formable flexible plastic material and including a flange portion extending in a closed loop around the container body at the open top end,
    a sealing cavity formed within the flange portion of the container body and extending throughout the closed loop defined by the flange portion and including an opening having a particular dimension across the opening and having an increased dimension across the opening at progressive positions into the cavity, relative to the dimension at the opening of the cavity, for a major portion of the depth of the opening,
    a cover for closing the open end of the container body, the cover being formed from the heat formable flexible plastic material and including a flange portion extending in a closed loop around the cover corresponding to the closed loop for the flange portion of the container body, and
    a sealing cavity formed within the flange portion of the cover and nested within the sealing cavity in the flange portion of the container when the cover seals the open end of the container body and complementary to the shape of the sealing cavity in the flange portion of the container body and providing laminar surface-to-surface contact between the mating surfaces of the sealing cavities throughout the surface areas defining the closed loop of the flange portion on the cover and the closed loop of the sealing cavity in the flange portion of the container.

2. The sterile container of claim 1 wherein the flange portions extend outwardly and the cavities are formed as integral portions within the flange portions.

3. The sterile container of claim 1 wherein the sealing cavity in the flange portion of the cover is formed in a shape complementary to the shape of the sealing cavity in the flange portion of the container body prior to the cover closing the open end of the container body.

4. The sterile container of claim 1 wherein the sealing cavity in the flange portion of the cover is formed in a shape complementary to the shape of the sealing cavity in the flange portion of the container body after the cover closes the open end of the container body.

5. The sterile container of claim 1 additionally including adhesive material between the nested sealing cavities throughout the closed loops of the cavities for providing a further seal between the sealing cavities.

6. The sterile container of claim 1 additionally including means coupled to the sealing cavities for providing for the imposition of a force in a direction to move the sealing cavities into laminar surface-to-surface contact with each other throughout the areas defining the closed loops of the sealing cavities.

7. The sterile container of claim 1 additionally including a gas pathway disposed in the sterile container and formed with a recess and an opening in the recess and further including first filter means located within the opening in the recess and a porous membrane forming second filter means and positioned adjacent the first filter means and disposed in the recess across the opening and locking the first filter means within the opening in the recess.

8. The sterile container of claim 7 wherein the gas pathway is formed in a bottom wall of the container body opposite the open end.

9. A container, including,
 a body portion formed from a particular heat formable flexible plastic material and provided with a first flange disposed in a closed loop around the container body and having a first cavity disposed in the flange around the closed loop,
 a cover portion formed from the particular heat formable plastic material and provided with a second flange disposed in the closed loop and having a second cavity complementary to the first cavity and disposed in the closed loop for nesting within the first cavity,
 the mating surfaces of the sealing cavities being disposed in laminar surface-to-surface contact throughout the closed loops, at least one of the body portion and the cover portion having the sealing cavity preformed in the following configuration,
 first and second oppositely disposed wall portions forming sidewalls for the sealing cavity,
 a bottom wall portion interconnecting the first and second wall portions and forming with the first and second wall portions a closed cavity having an open end opposite the bottom wall portion, and
 the first and second oppositely disposed wall portions diverging progressively outwardly in the distance between the first and second oppositely disposed wall portions for a major portion of the distance from the open end to the bottom wall portion.

10. The container of claim 9 wherein the complementary flanges extend outwardly from the body and cover portions and define the sealing cavities as being in integral relationship with the flanges.

11. The container of claim 9 wherein the sealing cavities in the flanges are preformed in the complementary configurations prior to the cover portion closing the body portion.

12. The container of claim 9 wherein the other of the sealing cavities in the flange is formed, after the cover portion closes the body portion, in the complementary configuration providing laminar surface-to-surface contact between the sealing cavities in the flanges throughout the closed loops of the sealing cavities.

13. The container of claim 9 additionally including an adhesive material located between the nested sealing cavities throughout the closed loops of the sealing cavities for providing a further seal between the sealing cavities.

14. The container of claim 9 additionally including means coupled to the sealing cavities for providing for the imposition of a force in a direction to move the sealing cavities into engagement with each other.

15. The container of claim 9 additionally including a gas pathway disposed in the sterile container and formed with a recess and an opening in the recess and further including first filter means located within the opening and a porous membrane forming second filter means and positioned in the recess adjacent the first filter means and across the opening and locking the first filter means within the opening.

* * * * *